United States Patent [19]

Preiss et al.

[11] 4,235,774
[45] Nov. 25, 1980

[54] PENICILLIN DERIVATIVES

[75] Inventors: Michael Preiss; Hans-Bodo König; Karl G. Metzger; Gunter Schmidt, all of Wuppertal, Fed. Rep. of Germany

[73] Assignee: Bayer Aktiengesellschaft, Leverkusen, Fed. Rep. of Germany

[21] Appl. No.: 11,347

[22] Filed: Feb. 12, 1979

[30] Foreign Application Priority Data

Mar. 8, 1978 [DE] Fed. Rep. of Germany ....... 2810083

[51] Int. Cl.³ ............................................ C07D 499/70
[52] U.S. Cl. ............................ 260/239.1; 424/248.51; 424/271; 424/250; 544/379; 548/247; 548/318

[58] Field of Search ...................... 260/239.1

[56] References Cited

U.S. PATENT DOCUMENTS

| 3,939,149 | 2/1976 | Konig et al. | 260/239.1 |
| 3,972,869 | 8/1976 | Konig et al. | 260/239.1 |
| 3,974,141 | 8/1976 | Konig et al. | 260/239.1 |
| 4,031,229 | 6/1977 | Konig et al. | 260/239.1 |

FOREIGN PATENT DOCUMENTS

| 2104579 | 8/1972 | Fed. Rep. of Germany . |
| 2104580 | 8/1972 | Fed. Rep. of Germany . |
| 2152968 | 5/1973 | Fed. Rep. of Germany . |
| 2152967 | 4/1973 | Fed. Rep. of Germany . |
| 2258973 | 6/1974 | Fed. Rep. of Germany . |
| 2407715 | 9/1975 | Fed. Rep. of Germany . |
| 2528078 | 1/1977 | Fed. Rep. of Germany . |
| 2528079 | 1/1977 | Fed. Rep. of Germany . |

OTHER PUBLICATIONS

Angewandte Chemie, 81, (1969), 543, at p. 7.

Primary Examiner—Natalie Trousof
Assistant Examiner—Vera C. Clarke
Attorney, Agent, or Firm—Sprung, Felfe, Horn, Lynch & Kramer

[57] ABSTRACT

New penicillin derivatives, or esters or salts thereof, of the formula

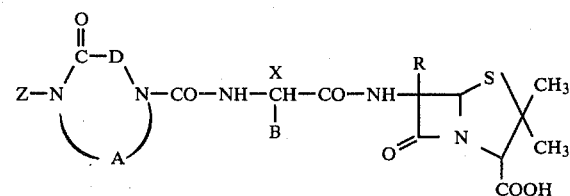

in which
R is H or alkoxy,
B is a heterocyclic radical,
A is an ethylene, trimethylene or o-phenylene radical,
D is —co— or a direct bond, and
Z is a hydrogen atom, an optionally substituted alkyl or alkenyl group, an optionally substituted cycloalkyl, cycloalkenyl or cycloalkadienyl group, an optionally substituted aryl group, an optionally substituted hetercyclyl group or an acyl radical.

11 Claims, No Drawings

PENICILLIN DERIVATIVES

The present invention relates to certain new β-lactam compounds, to a process for their production and to their use as antimicrobial agents and as agents for promoting the growth of animals and for improving feedstuff utilization in animals.

According to the present invention, we provide compounds which are β-lactams of the following general formula

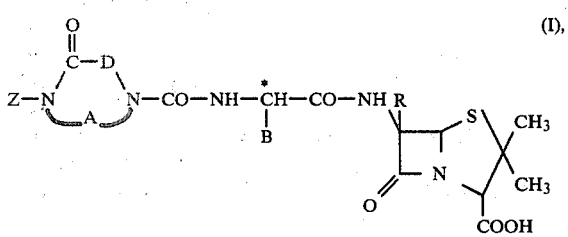

esters or salts thereof or compounds thereof in which the carboxyl group is protected by a protective group, in which R denotes a hydrogen atom or an alkoxy group, B denotes an optionally substituted furyl, pyrrolyl, pyrazolyl, imidazolyl, triazolyl, tetrazolyl, oxazolyl, isoxazolyl, oxdiazolyl, thiazolyl, 2-imino-$\Delta^4$-thiazolin-4-yl, isothiazolyl, thiadiazolyl, oxtriazolyl, thiatriazolyl, sydnonyl, pyridyl, pyrazinyl, pyridazinyl, pyrimidinyl, triazinyl, tetrazinyl or pyronyl group, A denotes an ethylene, trimethylene or o-phenylene radical, D denotes a carbonyl group or a direct bond and Z denotes a hydrogen atom, an optionally substituted alkyl or alkenyl group, an optionally substituted cycloalkyl group, a cycloalkenyl or cycloalkadienyl group, an optionally substituted aralkyl group, an optionally substituted aryl group, an optionally substituted heterocyclyl group, or an acyl radical.

Preferred groups R are, in particular, $C_1$ to $C_6$ alkoxy groups, especially $C_1$ to $C_4$ alkoxy groups.

Suitable substituents of the radicals B are halogen, such as fluorine, chlorine and bromine, alkyl with 1 to 6 C atoms, cyano, nitro, hydroxyl, amino, sulpho and methylsulphonyl; the radicals B can also be partially hydrogenated. The number of possible substituents is preferably 0 to 2. Preferred substituents are fluorine, chlorine, methyl and ethyl, cyano, hydroxyl and amino.

Optionally substituted alkyl Z denotes straight-chain or branched alkyl with preferably 1 to 6, especially 1 to 4, carbon atoms, which can preferably be substituted by 1 to 2 identical or different substituents $R^3$. Optionally substituted alkenyl Z is straight-chain or branched alkenyl with preferably 2 to 6, especially 2 to 4, carbon atoms, which can be substituted by 1 to 2 identical or different substituents $R^3$. Optionally substituted cycloalkyl, cycloalkenyl and cycloalkadienyl Z is monocyclic, bicyclic or tricyclic and preferably contains 3 to 10, especially 3, 5 or 6, carbon atoms, and can be substituted by 1 or 2 identical or different substituents $R^3$. Preferably, the alkyl, alkenyl, cycloalkyl, cycloalkenyl and cycloalkadienyl groups are unsubstituted or contain one substituent $R^3$.

$R^3$ preferably denotes halogen, especially fluorine, chlorine and bromine, amino, $C_1$ to $C_4$ alkylamino, preferably methylamino or ethylamino, di-($C_1$ to $C_4$ alkyl)-amino, preferably dimethylamino or diethylamino, pyrrolidyl, piperidyl, formylamino, ($C_1$ to $C_4$ alkyl)-carbonylamino, preferably acetylamino, N-($C_1$ to $C_4$ alkyl)-formylamino, preferably N-methyl-formylamino or N-ethyl-formylamino, N-($C_1$ to $C_4$ alkyl)-($C_1$ to $C_4$ alkyl)-carbonylamino, preferably N-ethyl-acetylamino, di-($C_1$ to $C_4$ alkyl)-methylimino, $C_1$ to $C_4$ alkylsulphonylamino, preferably methylsulphonylamino or ethylsulphonylamino, N-$C_1$ to $C_4$ alkyl-$C_1$ to $C_4$ alkylsulphonylamino, preferably N-methyl-methylsulphonylamino, hydroxysulphonylamino, N-$C_1$ to $C_4$ alkylhydroxysulphonylamino, preferably N-methylhydroxysulphonylamino or N-ethyl-hydroxysulphonylamino, amidino, di-($C_1$ to $C_4$ alkyl)-aminomethylimino, especially dimethylaminomethylimino, pyrrolidinylmethylimino, guanido, nitro, azido, hydroxy, $C_1$ to $C_4$ alkoxy, preferably methoxy or ethoxy, formyloxy, ($C_1$ to $C_4$ alkyl)-carbonyloxy, preferably acetoxy, ethylcarbonyloxy or tert.-butylcarbonyloxy, ($C_1$ to $C_4$ alkoxy)-carbonyloxy, preferably methoxycarbonyloxy, ethoxycarbonyloxy or tert.-butylbutoxycarbonyloxy, aminocarbonyloxy, ($C_1$ to $C_4$ alkylamino)-carbonyloxy, preferably methylaminocarbonyloxy or ethylaminocarbonyloxy, di-($C_1$ to $C_4$ alkyl)-aminocarbonyloxy, preferably dimethylaminocarbonyloxy or diethylaminocarbonyloxy, piperidinylcarbonyloxy, aminosulphonyloxy, $C_1$ to $C_4$ alkylaminosulphonyloxy, preferably methylaminosulphonyloxy or ethylaminosulphonyloxy, di-($C_1$ to $C_4$ alkyl)-aminosulphonyloxy, preferably methylaminosulphonyloxy or diethylaminosulphonyloxy, carboxy, aminocarbonyl, di-($C_1$ to $C_4$ alkyl)-aminocarbonyl, especially dimethylaminocarbonyl and diethylaminocarbonyl, formyl, hydroxysulphonyloxy, mercapto, $C_1$ to $C_4$ alkylmercapto, preferably methylmercapto, trifluoromethylmercapto, ethylmercapto or isopropylmercapto, $C_1$ to $C_4$ alkylsulphinyl, preferably methylsulphinyl or ethylsulphinyl, sulpho, $C_1$ to $C_4$ alkylsulphonyl, preferably methylsulphonyl, trifluoromethylsulphonyl or ethylsulphonyl, aminosulphonyl, $C_1$ to $C_4$ alkylaminosulphonyl, preferably methylaminosulphonyl or ethylaminosulphonyl, di-($C_1$ to $C_4$ alkyl)-aminosulphonyl, preferably dimethylaminosulphonyl or diethylaminosulphonyl, piperidinylsulphonyl, thiosulphato, phenoxy and - in the case of the cyclic radicals - alkyl with 1 to 6 carbon atoms, preferably methyl.

Optionally substituted aralkyl Z contains 6 or 10, especially 6, carbon atoms in the aryl radical and preferably 1 to 4, especially 1 or 2, carbon atoms in the alkyl part; the alkyl part can be straight-chain or branched and the aralkyl radical can carry 1 to 3 substituents $R^3$. Preferably the aralkyl radical is unsubstituted or contains one substituent $R^3$.

Optionally substituted aryl Z is, in particular, aryl with 6 to 10 carbon atoms, which can be substituted by 1 to 3 substituents $R^3$. In particular, aryl is phenyl or naphthyl optionally substituted by one substituent $R^3$.

Optionally substituted heterocyclyls Z are heteroparaffinic, hetero-aromatic and hetero-olefinic 5-membered to 7-membered, preferably 5-membered or 6-membered, rings with preferably 1 to 3, especially 1 or 2, identical or different hetero-atoms. Suitable hetero-atoms are oxygen, sulphur or nitrogen. Possible examples are optionally substituted thienyl, furyl, oxazolyl, isoxazolyl, thiazolyl, isothiazolyl, pyrrolyl, imidazolyl, pyrazolyl, oxadiazolyl, thiadiazolyl, triazolyl, oxtriazolyl, thiatriazolyl, tetrazolyl, pyridyl, pyrazinyl, pyrimidinyl, tetrahydrofuranyl, dioxanyl, pyrrolidinyl, piperidinyl, morpholinyl, pyron-2-yl and pyron-4-yl. Heterocyclyl Z can be substituted by 1 or more, preferably 1 to 3, especially 1 or 2, identical or different substituents $R^4$. Heterocyclyl Z which is unsubstituted or contains one substituent $R^4$ is very particularly preferred.

Where $R^4$ is bonded to a carbon atom, $R^4$ preferably denotes $C_1$ to $C_4$ alkyl, preferably methyl, ethyl or isopropyl, trifluoromethyl, halogen, preferably fluorine, chlorine or bromine, amino, $C_1$ to $C_4$ alkylamino, preferably methylamino or ethylamino, di-($C_1$ to $C_4$ alkyl)-amino, preferably dimethylamino or diethylamino, formylamino, acetylamino, methoxycarbonylamino, ethoxycarbonylamino, methylsulphonylamino, hydroxy, methoxy, ethoxy, methylmercapto, ethylmercapto, methylsulphonyl, methylsulphinyl, carboxy, sulpho, formyl, ($C_1$ to $C_4$ alkyl)-carbonyl, preferably acetyl, ($C_1$ to $C_4$ alkoxy)-carbonyl, preferably methoxycarbonyl or ethoxycarbonyl and cyano.

If $R^4$ is bonded to a nitrogen, $R^4$ denotes $C_1$ to $C_4$ alkyl, preferably methyl, ethyl, propyl or isopropyl, cyano, formyl, ($C_1$ to $C_4$ alkoxy)-carbonyl, preferably methoxycarbonyl, ethoxycarbonyl, isopropoxycarbonyl, tert.-butoxycarbonyl, aminocarbonyl, ($C_1$ to $C_4$ alkylamino)-carbonyl, preferably methylaminocarbonyl, ethylaminocarbonyl or isopropylaminocarbonyl and ($C_1$ to $C_4$ alkyl)-carbonyl, preferably acetyl, ethylcarbonyl or isopropylcarbonyl.

Acyl radicals Z are, in particular, optionally substituted alkylcarbonyl, arylcarbonyl, alkylsulphonyl, arylsulphonyl, alkoxycarbonyl, aminocarbonyl and aminosulphonyl. Optionally substituted alkylcarbonyl is, in particular, ($C_1$ to $C_4$ alkyl)-carbonyl. Optionally substituted arylcarbonyl is, in particular, phenylcarbonyl which is optionally substituted by one or more, preferably 1 to 3, especially 1 or 2, identical or different substituents $R^3$. Optionally substituted alkylsulphonyl is, in particular, $C_1$ to $C_4$ alkylsulphonyl. Optionally substituted arylsulphonyl is, in particular, phenylsulphonyl which is optionally substituted by one or more, preferably 1 to 3, especially 1 or 2, identical or different substituents $R^3$. Optionally substituted alkoxycarbonyl is preferably ($C_1$ to $C_4$ alkoxy)-carbonyl. Optionally substituted aminocarbonyl and aminosulphonyl is aminocarbonyl and aminosulphonyl optionally monosubstituted or disubstituted by $C_1$ to $C_4$ alkyl.

The compound of the formula (I) when a salt or ester is preferably in the form of a pharmaceutically usable ester group or a salt.

The compounds of the formula (I) can, in respect of the chirality center $\overset{*}{C}$, be in the two possible R- and S-configurations or in the form of mixtures of the diastereomers resulting therefrom. Compounds according to the invention in which $\overset{*}{C}$ is in the D-configuration (R-configuration) are preferred.

All crystal forms and hydrate forms of the compounds according to the invention, of the general formula (I), and of their salts, have the same type of antibacterial activity.

Preferred compounds within the formula (I) are those which in the form of the free acid correspond to the general formula

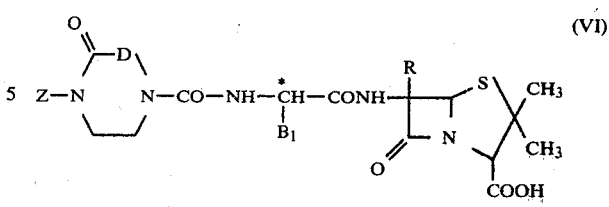

in which
Z and D have the above-mentioned meanings,
R denotes a hydrogen atom or a methoxy group, and
$B_1$ denotes a furyl, pyrrolyl, pyrazolyl, imidazolyl, thiazolyl, isothiazolyl, oxazolyl, isoxazolyl, thiadiazolyl, oxdiazolyl, iminothiazolyl, pyridyl, pyrimidinyl, pyridazinyl, pyrazinyl, sydnonyl, tetrazolyl or 2-imino-$\Delta^4$-thiazolin-4-yl group, and the chirality center $\overset{*}{C}$ is in the D-configuration (R-configuration).

The sodium salts of these compounds are particularly preferred.

Very particularly preferred compounds of the formula (VI) are those in which Z is a hydrogen atom or a methyl, ethyl, propyl, cyclopropyl, methylsulphonyl, ethylsulphonyl, phenylsulphonyl, methylaminosulphonyl or thiazolyl group.

The compounds according to the invention exhibit, in addition to good toleration and solubility, a broad antibacterial action, i.e. an action against several bacterial families from the Gram-negative range and against bacteria which form β-lactamase. Because of their powerful antibacterial properties and because of their ability to improve the growth of animals and feedstuff utilization in animals, the compounds according to the invention represent an advance in the art.

Compared to similar previously known compounds, for example those from DT-OS (German Published Specifications) Nos. 2,104,579, 2,104,580, 2,152,967, 2,152,968, 2,258,973, 2,407,715, 2,528,078 and 2,528,079, and from U.S. Pat. Nos. 3,974,141, 3,983,105, 3,972,869 and 4,031,229, the compounds according to the invention are distinguished by higher activity and/or better toleration.

According to the present invention, are further provided a process for the production of β-lactam compounds of the formula (I) in which compounds which, in the form of the free acid, correspond to the general formula

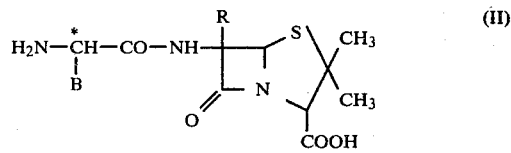

in which
R, B and $\overset{*}{C}$ have the above-mentioned meanings, are reacted with compounds of the general formula

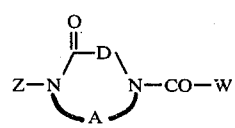

in which

Z, D and A have the above-mentioned meanings and W represents a nucleofugic leaving group, in the presence of a solvent and, if appropriate, of an acid-binding agent, at temperatures of −20° C. to +50° C., and, if desired, the resulting β-lactam compounds are converted to their salts or esters, or, if desired, the free acids are prepared from the salts obtained.

Nucleofugic leaving groups in the definition of W are to be understood as all nucleofugic groups usually employed in organic chemistry and above all those which are described in Angewandte Chemie, 81 (1969), 543. Preferably used nucleofugic leaving groups are halogen atoms and azide groups.

The compounds according to the invention, of the formula (I), wherein R represents alkoxy, can also be prepared by alkoxylation of the corresponding compounds wherein R denotes hydrogen, in which case it is advantageous to use, for the alkoxylation, those compounds in which the carboxyl group is protected by a protective group.

The compounds of the formula (I) can furthermore be obtained by reacting compounds of the formula (IV)

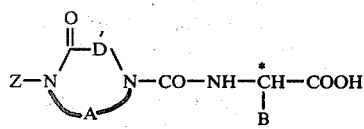

wherein B, D, A and Z have the above-mentioned meaning and the carboxyl group is activated by the methods of peptide chemistry, with compounds which in the form of the free acid correspond to the formula (V)

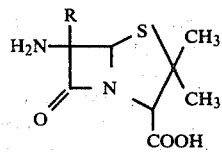

The compounds of the general formula (II) used as starting materials are already known or are obtainable in accordance with known methods. All crystal forms, hydrate forms and salts of the compounds of the general formula (II) are suitable starting materials for the process according to the invention.

The following may be mentioned as examples: 6-(α-aminofuryl)-acetamido-penicillanic acid, 6-[α-amino-(2-imino-Δ$^4$-thiazolidin-4-yl)]-acetamidopenicillanic acid, 6-[α-amino-(5-methylisoxazol-3-yl)]-acetamido-penicillanic acid and 6-(α-aminopyrid-3-yl)-acetamidopenicillanic acid. Suitable salts of the compounds of the formula (II) are preferably salts with bases which are listed as being suitable for forming salts with compounds of the formula (I). The disodium salts are particularly preferred.

The compounds of the general formula (III) used as starting materials are obtainable in accordance with known methods (DE-OS (German Published Specification) No. 2,528,078, and 2,152,967).

The following may be mentioned as examples of the starting compounds according to the invention, of the general formula (III): 1-chlorocarbonyl-2-oxo-3-methylsulphonylimidazoline, 1-azidocarbonyl-2-oxo-3-methylsulphonylimidazoline, 1-chlorocarbonyl-2-oxoimidazoline, 1-chlorocarbonyl-2-oxo-3-cyclopropyl-imidazoline and 1-chlorocarbonyl-2,3-dioxo-4-ethyl-piperazine.

Those compounds of the general formula (III), in which W is azide, are obtained in the usual manner, for example from the corresponding halogen compounds by reaction with alkali metal azides.

Suitable diluents for the process according to the invention are water and all inert organic solvents, preferably those which are water-miscible. These include, above all, $C_1$ to $C_4$ dialkyl ketones, for example acetone and methyl ethyl ketone, cyclic ethers, for example tetrahydrofuran and dioxane, nitriles, for example acetonitrile, lower dialkylformamides, for example dimethylformamide, lower alkanols, for example ethanol and isopropanol, and dimethylsulphoxide. These solvents can also be used as mixtures with one another or as any desired mixtures of one or more of these solvents with water. Accordingly, the process according to the invention can be carried out in the presence of: (a) water alone, (b) one or more organic solvents alone or (c) water and one or more organic solvents. If, because of the presence of water, it is possible to measure the pH during the reaction according to the invention, the pH of the reaction mixture is preferably kept between 6.5 and 7.5 by adding bases or by using buffer mixtures. However, the process according to the invention can also be carried out very successfully in a different pH range, for example between 4.5 and 9.0 or at pH 2.0 to 4.5. Furthermore it is possible to carry out the reaction in water-immiscible solvents, for example halogenated hydrocarbons, such as chloroform or methylene chloride, with addition of organic bases, preferably lower alkylamines, for example triethylamine or diethylamine, or cyclic bases, for example N-ethylpiperidine. The reaction can also be carried out in a mixture of water and a water-immiscible solvent, such as, for example, lower alkyl ethers, such as diethyl ether, halogenated hydrocarbons, such as chloroform and methylene chloride, carbon disulphide, isobutyl methyl ketone, esters, such as ethyl acetate, or aromatic hydrocarbons, such as benzene, in which case it is advantageous to stir the mixture vigorously and to keep the pH value between 4.5 and 9.0 or, for example, 2.0 and 4.5, by adding bases or using customary buffer solutions, for example phosphate, acetate or citrate buffers. However, the reaction can also be carried out in water alone, in the absence of organic solvents, in the presence of an organic or inorganic base, or with addition of customary buffer materials.

Acid-binding agents which can be used are all acid binders usually employed in the chemistry of the antibiotics. These include inorganic bases and organic bases which are difficult to acylate, for example due to steric hindrance. Sodium hydroxide and potassium hydroxide may be mentioned as examples of inorganic bases. Suitable organic bases are virtually all open-chain or cyclic amines which cannot be acylated, or can only be acylated with difficulty, and also hetero-aromatic bases. Examples of bases which may be mentioned are tertiary amines, preferably lower alkylamines, for example triethylamine and/or cyclic bases, for example pyridine, and - as a secondary amine which is difficult to acylate - dicyclohexylamine.

In the process according to the invention, the addition of a base is only necessary if acid compounds are formed during the reaction, for example if W represents halogen or azide.

The reaction temperatures can be varied within a substantial range. In general, the reaction is carried out at between about −20° C. and about +50° C., preferably between 0° and +20° C. As with most chemical reactions, it is however in principle also possible to use higher or lower temperatures.

The reaction can be carried out under normal pressure but also under reduced pressure or superatmospheric pressure. In general, it is carried out under normal pressure.

In carrying out the process according to the invention, the proportions of the reactants of the formula (II) and (III) can be varied within wide limits without adversely affecting the result. The starting materials can, for example, be reacted with one another in equimolecular amounts. However, it can be advantageous to use one of the two reactants in excess in order thereby to facilitate the purification, or pure preparation, of the desired penicillin and to increase the yield.

For example, the reactants of the general formula (II) can be employed in an excess of 0.1 to 0.3 mol equivalent, and less decomposition of the reactants of the general formula (III) in an aqueous solvent mixture can thereby be achieved. The excess of the reactants of the general formula (II) can be removed easily when working up the reaction mixture, because of the good solubility in aqueous mineral acids.

On the other hand, it is also possible to employ, with advantage, the reactants of the general formula (III) in an excess of, for example, 0.1 to 1.0 mol equivalent. This results in better utilization of the reactants of the general formula (II) and compensates for the decomposition of the reactants of the general formula (III) which takes place as a side reaction in aqueous solvents. Since the compounds of the general formula (III), added in excess, are rapidly converted, in water, into neutral nitrogen-containing heterocyclic compounds, which can be removed easily, the purity of the antibiotics is hardly impaired by such an excess.

The amount of the bases which may be used is determined, for example, by the desire to maintain a particular pH value. Where a pH measurement and adjustment is not carried out, or is not possible or meaningful because of the absence of sufficient amounts of water in the diluent, preferably 2 mol equivalents of base are added.

The working up of the reaction mixtures in order to prepare the compounds according to the invention and their salts is in every case carried out in the manner generally known for such compounds. The isolation and purification of the compounds according to the invention, and the liberation of the free acids from salts, or the conversion of the free acids into salts, are also carried out in accordance with generally customary methods of organic chemistry, which are familiar to any expert.

As an alternative, the compounds of the formula (I), in which R denotes alkoxy, can also be obtained by alkoxylating the corresponding hydrogen derivatives (R=H), during which process the carboxyl group is protected by a suitable protective group, for example an easily removable ester-forming group or an acetoxymethyl group, or is in the form of a salt, preferably an alkali metal salt or alkaline earth metal salt.

In this process, a β-lactam compound of the formula (I), in which R denotes hydrogen, is reacted with 2 to 10 equivalents of a base per equivalent of β-lactam compound, in the presence of an excess of an alkanol in an inert organic solvent, between about 1 and about 8 equivalents of a N-halogenating agent are added and the compound of the formula (I), in which R denotes alkoxy, is isolated, where appropriate after first splitting off the acid protective group, converting the compound into a salt or converting it to a pharmaceutically usable ester.

In this process according to the invention, the N-halogenating agents used are preferably compounds which transfer positive chlorine, such as t-butyl hypochlorite or chloroacetamide.

Suitable bases are complex and simple bases, but preferably simple alkali metal hydrides and alkaline earth metal hydrides, and organo-metallic compounds, as well as Grignard compounds. Examples which may be mentioned are lithium hydride, sodium hydride, butyl-lithium, phenyl-lithium, alkyl-magnesium bromides, for example methyl-magnesium bromide, or other known acid-binding agents, such as alkali metal and alkaline earth metal alcoholates or carbonates, alkali metal and alkaline earth metal bicarbonates or oxides, such as, for example, sodium carbonate, or other acid-binding agents, such as borax or open-chain or cyclic organic bases, such as trialkylamines or aralkylamines or cyclic amidines, such as 2,3,4,6,7,8-hexahydro-pyrrolo[1,2-a]pyrimidine (DBN) or 2,3,4,6,7,8,9,10-octahydro-pyrimido[1,2-a]azepine (DBU).

Examples of suitable solvents are open-chain or cyclic ethers, aliphatic and aromatic hydrocarbons or halohydrocarbons or the alcohols R'OH. Tetrahydrofuran is particularly suitable.

Pharmaceutically usable salts of the compounds of the formula (I) are salts of these compounds with inorganic and organic bases, the salts being formed at the acid carboxyl group or at the acid carboxyl groups and sulphonic acid groups. Bases which can be used for this purpose are all bases usually employed in pharmaceutical chemistry, especially in the chemistry of the antibiotics. Examples of inorganic bases which may be mentioned are alkali metal hydroxides and alkaline earth metal hydroxides, alkali metal carbonates and alkaline earth metal carbonates and alkali metal bicarbonates, such as sodium hydroxide and potassium hydroxide, calcium hydroxide and magnesium hydroxide, sodium carbonate and potassium carbonate, calcium carbonate, sodium bicarbonate and potassium bicarbonate, aluminum hydroxide and ammonium hydroxide. Organic amines which can be employed are primary, secondary and tertiary aliphatic amines as well as heterocyclic amines. Examples which may be mentioned are dialkylamines and trialkylamines, for example diethylamine, triethylamine, tri-β-hydroxyethylamine, procaine, dibenzylamine, N,N′-dibenzylethylenediamine, N-benzyl-β-phenyl-ethylamine, N-methylmorpholine, N-ethylmorpholine, 1-ephenamine, dehydroabietylamine, N,N′-bis-dehydroabietylethylenediamine and $N-C_1$ to $C_4$ alkylpiperidine. So-called basic aminoacids, such as lysine or arginine, can also be used advantageously as bases. The disodium salts are particularly preferred salts.

The active compounds according to the invention display a powerful and broad antimicrobial activity, coupled with low toxicity. These properties enable them to be used as chemotherapeutic active compounds in medicine and as substances for preserving inorganic and organic materials, especially organic materials of all kinds, for example polymers, lubricants, paints, fibers, leather, paper and timber, and foodstuffs and water.

The active compounds according to the invention are active against a very broad spectrum of micro-organisms. With their aid it is possible to combat Gram-negative and Gram-positive bacteria and bacteria-like micro-organisms and to prevent, alleviate and/or cure diseases caused by these pathogens.

The active compounds according to the invention are particularly active against bacteria and bacteria-like-micro-organisms. They are therefore particularly suitable, in human medicine and veterinary medicine, for the prophylaxis and chemotherapy of local and systemic infections caused by these pathogens.

For example, local and/or systemic diseases which are caused by the following pathogens or by mixtures of the following pathogens can be treated and/or prevented:

Micrococcaceae, such as Staphylococci, for example *Staphylococcus aureus, Staph. epidermidis* and *Staph. aerogenes*, and *Gaffkya tetragena* (Staph. = Staphylococcus); Lactobacteriaceae, such as Streptococci, for example *Streptococcus pyogenes*, α- and β-haemolysing Streptococci, non-(γ)-haemolysing Streptococci, *Str. viridans, Str. faecalis* (Enterococci), *Str. agalactiae, Str. lactis, Str. equi* and *Str. anaerobis*, and *Diplococcus pneumoniae* (Pnuemococci) (Str. = Streptococcus); Neisseriaceae, such as Neisseriae, for example *Neisseria gonorrhoeae* (Gonococci), *N. meningitidis* (Meningococci), *N. catarrhalis* and *N. flava* (N. = Neisseria); and Corynebacteriaceae, such as Corynebacteria, for example *Corynebacterium diphtheriae, C. pyogenes, C. diphtheroides, C. acnes, C. parvum, C. bovis, C. renale, C. ovis* and *C. murisepticum*.

Mycobacteriaceae, such as pathogens of mycobacterioses, for example *Mycobacterium tuberculosis, M. bovis, M. avium*, so-called atypical mycobacteria of Runyon groups I, II, III and IV and *M. leprae* (M. = Mycobacterium);

Enterobacteriaceae, such as Escherichiae bacteria of the Coli group; Escherichia bacteria, for example *Escherichia coli*, Enterobacter bacteria, for example *E. aerogenes* and *E. cloacae*, Klebsiella bacteria, for example *K. pneumoniae* and *K. ozaenae*, Erwiniae, for example *Erwinia spec.*, and Serratia, for example *Serratia marcescens* (E. = Enterobacter) (K. = Klebsiella), Proteae bacteria of the Proteus group: Proteus, for example *Proteus vulgaris, Pr. morganii, Pr. rettgeri* and *Pr. mirabilis*, and Providencia, for example Providencia sp., (Pr. = Proteus), and Salmonelleae: Salmonella bacteria, for example *Salmonella paratyphi A* and *B, S. typhi, S. enteritidis, S. cholerae suis* and *S. typhimurium* (S. = Salmonella), and Shigella bacteria, for example *Shigella dysenteriae, Sh. ambigua, Sh. flexneri, Sh. boydii* and *Sh. sonnei* (Sh. = Shigella);

Pseudomonadaceae, such as Pseudomonas bacteria, for example *Pseudomonas aeruginosa* and *Ps. pseudomallei* (Ps. = Pseudomonas), and Aeromonas bacteria, for example *Aeromonas liquefaciens* and *A. hydrophila* (A.- = Aeromonas);

Parvobacteriaceae, such as Pasteurella bacteria, for example *Pasteurella multocida, Past. pestis* (*Yersinia*) and *Past. pseudotuberculosis* (Past. = Pasteurella), Haemophilus bacteria, for example *Haemophilus influenzae, H. ducreyi, H. suis, H. canis* and *H. aegypitcus* (H. = Haemophilus), and Bordetella bacteria, for example *B. bronchiseptica* (B. = Bordetella);

Bacteroidaceae, such as Bacteroides bacteria, for example *Bacteroides fragilis* and *B. serpens* (B. = Bacteroides), Fusiforme bacteria, for example *Fusobacterium fusiforme*, and Sphaerophorus bacteria, for example *Sphaerophorus necrophorus, Sph. necroticus* and *Sph. pyrogenes* (Sph. = Sphaerophorus);

Bacillaceae, such as aerobic spore-forming Bacillaceae, for example *Bacillus anthracis, B. subtilis* and *B. cereus* (B. = Bacillus), and anaerobic spore-forming Clostridia, for example *Clostridium perfringens, Cl. septicium, Cl. oedematiens, Cl. histolyticum, Cl. tetani* and *Cl. botulinum* (Cl. = Clostridium).

The above list of pathogens is purely illustrative and is in no way to be interpreted as restrictive.

Examples which may be mentioned of diseases which can be prevented, alleviated and/or cured by the active compounds according to the invention are: diseases of the respiratory passages and of the pharyngeal cavity; otitis; pharyngitis; pneumonia, peritonitis; pyelonephritis; cystitis; endocarditis; systemic infections; bronchitis; arthritis and local infections.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc. calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbitol and sorbitan esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for administration of the medicaments of the invention is 250 mg to 50 g, preferably 1 g to 10 g, of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramusclarly, intraperitoneally, subcutaneously intravenously), rectally or locally, preferably orally or parenterally. Preferred pharmaceutical compositions and medicaments are therefore those adapted for administration such as oral or parenteral administration. Administration in the method of the invention is preferably oral or parenteral administration.

In general it has proved advantageous to administer amounts of from 5 mg to 1,000 mg/kg, preferably 20 to 200 mg/kg, of body weight per day to achieve effective results. An individual administration contains the active compound or compounds according to the invention, preferably in amounts of from 1 to 250, preferably 10 to 100 mg/kg of body weight. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other bases the upper limit mentioned must be exceeded to achieve the desired results. Where larger amounts are administered it can be advisable to divide these into several individual administrations over the course of the day.

When used as feedstuff additives, the new compounds can be administered in the customary concentrations and formulations together with the feedstuff or with feedstuff formulations or with the drinking water. By this means it is possible to prevent, alleviate and/or cure an infection by Gram-negative or Gram-positive bacteria and also to achieve promotion of growth and better utilisation of the feedstuff. According to the invention there is therefore provided a medicated fodder comprising a compound of the invention and a nutricious material.

The new penicillins are distinguished by powerful antibacterial actions, which have been tested in vivo and in vitro.

In order to broaden the spectrum of action and to achieve a more powerful action, especially in the case of β-lactamase-forming bacteria, the penicillins according to the invention can be combined with other antimicrobial active compounds, for example with penicillins which are particularly penicillinase-resistant. Such a combination would be, for example, one with oxacillin or dicloxacillin.

In order to broaden the spectrum of action and to achieve a more powerful action, the penicillins according to the invention can also be combined with aminoglycoside antibiotics, such as gentamicin, kanamicin, sisomicin, amikacin or tobramicin, and lactamase inhibitors, such as clavulanic acid and clavulanic acid derivatives.

The activity of the β-lactam antibiotics according to the invention can be demonstrated, by way of example, by the following in vitro experiments:

1. In vitro experiments

Examples 1 and 2 which can be regarded as typical representatives of the compounds according to the invention, were diluted to a content of 100 μg/ml with Müller-Hinton nutrient broth, 0.1% of glucose being added. In each case, the nutrient solution contained $1 \times 10^5$ to $2 \times 10^5$ bacteria per milliliter. The small tubes containing this batch were in each case incubated for 24 hours and the degree of turbidity was then determined. Freedom from turbidity indicates action. At a dosage of 100 μg/ml, the following bacteria cultures were free from turbidity (sp.=species):

*Klebsiella pneumoniae; Enterobacter aerogenes* sp.; *Providencia; Serratia marcescens; E. coli* BE; *Salmonella* sp.; *Shigella* sp.; *Proteus*, indole-negative and indole-positive; *Pasteurella pseudotuberculosis; Brucella* sp.; *Haemophilus influenzae; Bordetella bronchiseptica; Staphylococcus aureus* 133; *Neisseria catarrhalis* sp.; *Diplococcus pneumoniae* sp.; *Streptococcus pyogenes* W.; *Enterococcus* sp.; *Lactobacillus* sp.; *Corynebacterium diphteriae gravis; Corynebacterium pyogenes* M; *Clostridium tetani* and *Pseudomonas aeruginosa* sp.

The following examples illustrate the preparation of individual compounds of the invention.

EXAMPLE 1

Sodium 6-{α-[(2-oxo-imidazolidin-1-yl)-carbonylamino]-furyl-2-acetamido}-penicillanate

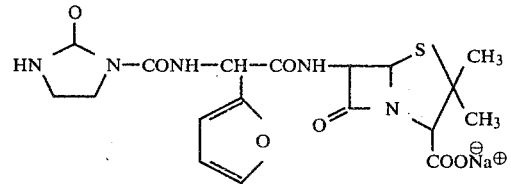

A solution of 2.4 g of 6-(α-amino-furylacetamido)-penicillanic acid (U.S. Pat. No. 3,120,514) in 50 ml of 80% strength aqueous tetrahydrofuran (THF) is cooled to 5° C. and brought to pH 8 with 1 N sodium hydroxide solution. 1.4 g of 1-chlorocarbonyl-2-oxo-imidazole are added incrementally while the pH is kept at 7.5 with 0.5 N sodium hydroxide solution. When the pH value is constant, 50 ml of water are added and the THF is distilled off in vacuo. The aqueous solution is extracted with ethyl acetate, cooled to 5° C., covered with 150 ml of ethyl acetate, acidified with 1 N hydrochloric acid, and extracted by shaking; the organic phase is separated off, dried over $MgSO_4$ and concentrated. The residue is suspended in 35 ml of water and dissolved by means of 0.5 N sodium hydroxide solution, and this solution is lyophilized. 2.5 g of sodium salt of decomposition point 200° to 210° C. are obtained. IR (paraffin oil): 3,200, 1,770, 1,705 and 1,600 cm$^{-1}$.

EXAMPLE 2

Sodium 6-{α-[(2-oxo-3-methylsulphonyl-imidazolidin-1-yl)-carbonylamino]-furyl-2-acetamido}-pencillanate

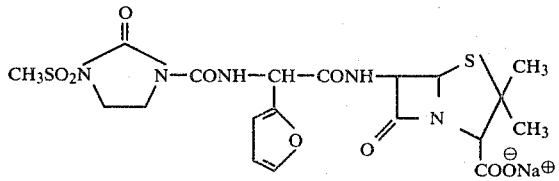

2.4 g of 6-(α-amino-furylacetamido)-pencillanic acid and 2.3 g of 1-chlorocarbonyl-2-oxo-3-methylsulphonylimidazole are reacted, and worked up, as in Example 1. 3.2 g of decomposition point 195° to 204° C. are obtained. IR (KBr): 3,420, 1,750, 1,660, 1,590, 1,525, 1,380 and 1,165 cm$^{-1}$.

If D,L-6-(α-amino-furfurylacetamido)-penicillanic acid is used as the starting material, the penicillins of Example 1 and 2 are obtained as diastereomer mixtures which can be separated into the α-D-form and α-L-form by, for example, preparative high pressure liquid chromatography.

EXAMPLE 3

(a) Preparation of 2-(2-oxo-3-methylsulphonyl-imidazolidin-1-yl-carbonylamino)-(5-methyl-isoxazol-3-yl)-acetic acid

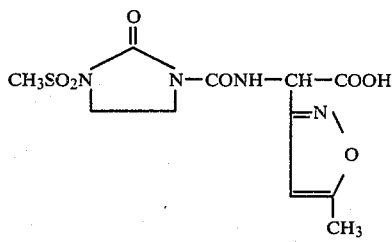

1 N Sodium hydroxide solution is added to a suspension of 8.5 g of 2-(5-methylisoxazol-3-yl)-glycine in 150 ml of water until the material has dissolved, and the pH is then brought to 7.6. 12.3 g of 1-chlorocarbonyl-2-oxo-3-methylsulphonyl-imidazolidine are then added in portions, the pH being kept at 7.5–7.7 by dropwise addition of 1 N sodium hydroxide solution. The solution is filtered, acidified and extracted with ethyl acetate. The ethyl acetate phases are dried over sodium sulphate and concentrated. 11.0 g of decomposition point 168° C. result; the material is dried in a high vacuum at 100° C.

IR (KBr): 3,326, 1,737, 1,536, 1,396 and 1,168 $cm^{-1}$.

(b) Preparation of sodium 6-{α-[(2-oxo-3-methylsulphonyl-imidazolidin-1-yl)-carbonylamino]-(5-methyl-isoxazol-3-yl)-acetamido}-penicillanate

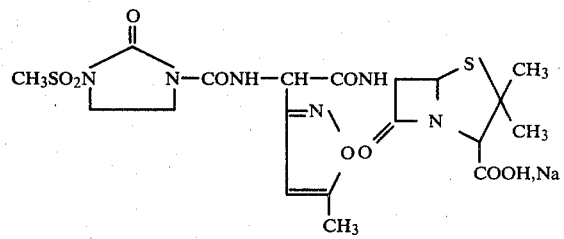

1.1 g of triethylamine are added to a suspension of 3.8 g of 2-(2-oxo-3-methylsulphonyl-imidazolidin-1-yl)-carbonylamino-(5-methyl-isoxazol-3-yl)-acetic acid in 100 ml of absolute acetone. The mixture is stirred for 30 minutes and is then cooled to −40° C., 0.1 g of 3-dimethylaminopropan-1-ol and 0.5 g of ethyl chloroformate are added and the batch is stirred for 20 minutes at −20° C. and then cooled to −50° C. A solution, cooled to −10° C., of 3.6 g of 6-aminopenicillanic acid in 15 ml of water and 10 ml of acetone (dissolved with 2 N sodium hydroxide solution at 0° C.) is added all at once. The mixture is warmed to room temperature, 35 ml of water are added, the acetone is stripped off, water is added to bring the volume to 120 ml, the batch is filtered and acidified to pH 2, and the product is filtered off, suspended in water, dissolved by means of 2 N sodium hydroxide solution to give a solution of about 10 percent strength, and freeze-dried. 3.6 g of decomposition point 186°–205° C. are obtained.

IR (KBr): 3,440, 1,770, 1,730, 1,675, 1,605, 1,395 and 1,167 $cm^{-1}$.

EXAMPLE 4

(a) Preparation of 2-(2,3-dioxo-4-ethyl-piperazin-1-yl-carbonylamino)-furyl-2-acetic acid

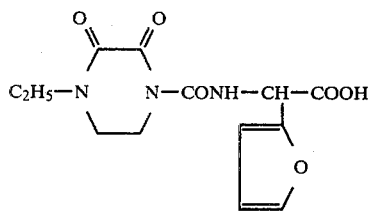

13.8 g of 2-furylglycine in 250 ml of water are reacted with 20.0 g of 1-chlorocarbonyl-2,3-dioxo-4-ethyl-piperazine as in Example 3(a). 13.2 g of decomposition point 202°–207° C. are obtained.

IR (KBr): 3,279, 1,745, 1,713, 1,659, 1,491, 1,391, 1,287, 1,180 and 756 $cm^{-1}$.

(b) Preparation of sodium 6-{α-[(2,3-dioxo-4-ethyl-piperazin-1-yl)-carbonylamino]-furyl-2-acetamido}-pencillanate

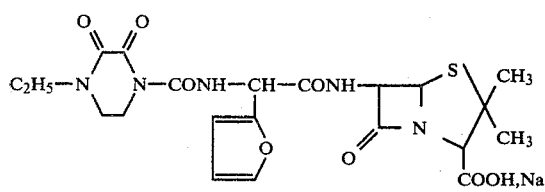

3.4 g of 2-(2,3-dioxo-4-ethyl-piperazin-1-yl-carbonylamino)-furyl-2-acetic acid are reacted with 3.6 of 6-aminopenicillanic acid as in Example 3(b). 2.8 g of decomposition point 215°–220° C. are obtained.

IR (KBr): 3,410, 1,769, 1,607, 1,459, 1,339 and 1,310 $cm^{-1}$.

EXAMPLE 5

(a) Preparation of 2-(2-oxo-3-methylsulphonyl-imidazolidin-1-yl-carbonylamino)-(5-methylfuryl-2)-acetic acid

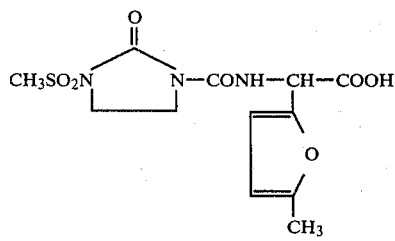

13.7 g of 2-(methylfuryl)-glycine (prepared like 2-furylglycine), in 250 ml of water are reacted with 1-chlorocarbonyl-2-oxo-3-methylsulphonyl-imidazolidine as in Example 3(a). On acidification, the product precipitates and is filtered off. 12.8 g of decomposition point 184°–189° C. are obtained.

IR (KBr): 3,987, 1,745, 1,661, 1,548, 1,478, 1,392, 1,344 and 1,164 $cm^{-1}$.

(b) Preparation of sodium 6-{α-[(2-oxo-3-methylsulphonyl-imidazolidin-1-yl)-carbonylamino]-(5-methyl-furyl-2-)acetamido}-penicillanate

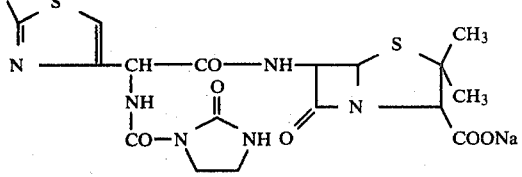

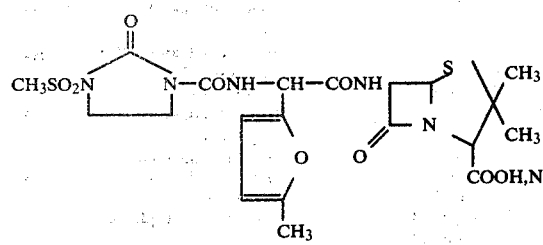

3.8 g of 2-(2-oxo-3-methylsulphonyl-imidazolidin-1-yl-carbonylamino)-(5-methylfuryl-2)-acetic acid are reacted with 2.5 g of 6-aminopenicillanic acid as in Example 3(b). 3.8 g of decomposition point 193°–195° C. are obtained.

IR (KBr): 3,430, 1,766, 1,731, 1,677, 1,611, 1,520, 1,478, 1,394 and 1,71 cm$^{-1}$.

EXAMPLE 6

(a) Preparation of 2-(2-oxo-imidazolidin-1-yl-carbonylamino)-2-(2-benzyloxycarbonylamino-thiazol-4-yl)-acetic acid

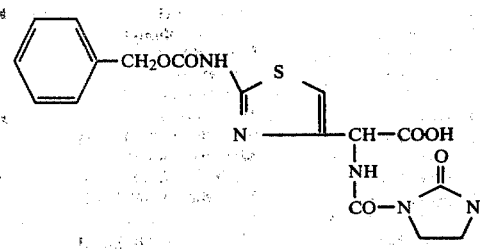

13.5 g of α-amino-α-(2-benzyloxycarbonylamino-thiazol-4-yl)-acetic acid dihydrate are suspended in a mixture of 100 ml water and 100 ml of THF and dissolved with 2 N-sodium hydroxide solution at a pH-value of 7.8. 6.4 g 1-chloro-carbonyl-2-oxoimidazolidine are added in portions during 30 minutes at 0° C. and a pH-value of 7.5 to 7.8. Subsequently the solution is stirred at room temperature for 2 hours. During this time the pH-value is kept at 7.5 by addition of 2 N sodium hydroxide solution. Then THF is distilled off, 200 ml of water are added to the remaining solution and the product is extracted with ethyl acetate. The aqueous phase is acidified to pH 2 by 2 N hydrochloric acid and extracted several times with ethyl acetate. The combined ethyl acetate phases are washed with sodium chloride containing water, dried over sodium sulphate and the solvent is distilled off. 9.5 g (58% of theory) are obtained.

(b) Preparation of sodium 6-{2-[(2-oxo-imidazolidin-1-yl)-carbonyl amino]-2(benzyloxycarbonylamino-thiazol-4-yl)-acetamido}-penicillinate 9.4 g of 2-(2-Oxo-imidazolidin-1-yl-carbonylamino)-2-(2-benzyloxycarbonylamino-thiazol-4-yl)-acetic acid in 60 ml THF and 60 ml DMF are treated with 32 ml of triethylamine and 4 drops of N-methyl morpholine. At −20° C. 2.94 ml of isobutyl chloroformate are added under stirring. After 40 minutes at −15° to −10° C. a cooled solution of the sodium salt of 6-aminopenicillanic acid—prepared from 4.85 g of 6-aminopenicillanic acid—is added. The solution is warmed to 10°–15° C. during 2 hours at a pH-value of 7.1. Then the solution is treated with 150 ml of water, the pH is adjusted to 7.6 and the solution is washed twice with ethyl acetate. The aqueous phase is acidified at 0° C. with 2 N hydrochloric acid and extracted by ethyl acetate. The ethyl acetate phases are washed with sodium chloride solution, dried and evaporated in vacuo. From the residue the sodium salt is prepared with a 1 M solution of sodium-2-ethyl hexanoate in methanolic diethyl ether. 9.5 g (63% of theory) are obtained.

Preparation of sodium-6-{2-[(2-oxo-imidazolidine-1-yl)-carbonylamino]-2-(2-amino-thiazol-4-yl)-acetamido}-penicillinate

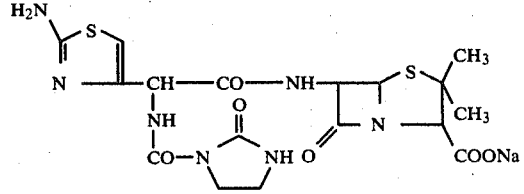

9.5 g sodium 6-{2-[(2-oxo-imidazolidin-1-yl)-carbonylamino]-2-(2-benzyloxycarbonylamino-thiazol-4-yl)-acetamido}-penicillinate are dissolved in 200 ml of water and hydrogenated in a prehydrogenated aqueous solution over 40 g of a palladium-catalyst. After 1 hour the catalyst is separated off and the solution freeze-dried. 3.4 g (43% of theory) are obtained.

$^1$H-NMR(CD$_3$OD; 100 MHz): δ=1.55–1.60 (2α-CH$_3$, 2β-CH$_3$), 3.37–3.56 (m, 2H, imidazolidinone), 3.79–4.0 (m, 2H, imidazolidinone), 4.2 (s, 3-H), 5.44–5.53 (d, 5-H, 6-H), 6.52 ppm (s, 1-thiazole-H).

EXAMPLE 7

(a)
2-(2-Oxo-3-methylsulfonyl-imidazolidin-1-yl-carbonylamino)-2-(2-benzyloxycarbonylamino-thiazol-4-yl) acetic acid

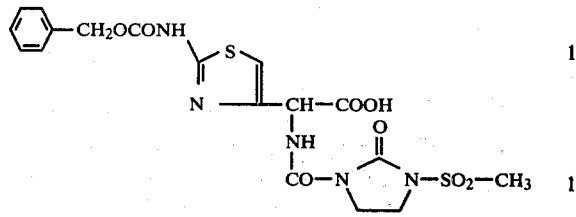

The compound is prepared analogously to Example 6 (a) from 15 g of α-amino-α-(2-benzyloxycarbonylamino-thiazol-4-yl)-acetic acid dihydrate in THF/water (1:1) and 10.9 g 1-chlorocarbonyl-2-oxo-3-methylsulfonyl-imidazolidine in a pH-range from 7.5 to 8.0. 14.1 g (65% of theory) are obtained.

(b)
Sodium-6-{2-[2-oxo-3-methylsulfonyl-imidazolidin-1-yl)-carboxylamino]-2-(2-benzyloxycarbonylamino-thiazol-4-yl)-acetamido}-penicillinate

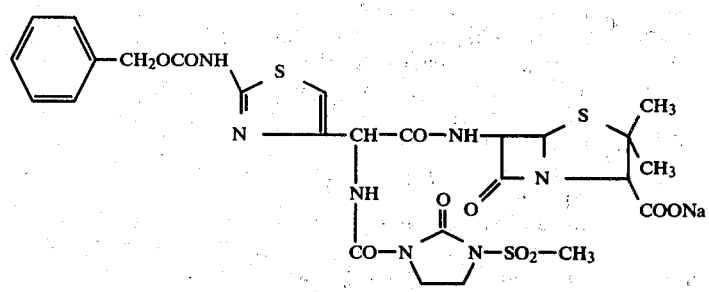

14.1 g of the compound of Example 7(a) are treated with 3.98 ml triethylamine under addition of 5 drops N-methylmorpholine and 3.74 ml of isobutyl chloroformate and then reacted with 6.14 g 6-aminopenicillanic acid analogous to Example 6(b). 16.1 g (77% of theory) are obtained.

(c)
Sodium-6-{2-[(2-oxo-3-methylsulfonyl-imidazolidin-1-yl)-carbonylamino]-2-(2-amino-thiazol-4-yl)acetamido}-penicillinate

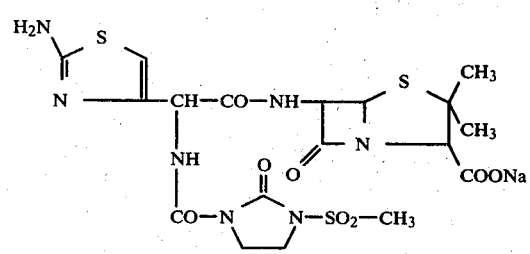

14 g of the compound of Example 7(b) are analogously to Example 6(c) hydrogenated in water over 40 g of a palladium catalyst. 8 g (70% of theory) are obtained.

$^1$H-NMR (CD$_3$OD, 100 MHz): δ=1.52–1.60 (2α-CH$_3$, 2β-CH$_3$), 3.32 (s, 3H, methylsulfonyl), 3.9 (s, 4H, imidazolidine-H), 4.17 (s, 3-H), 5.48 (s, 5-H, 6-H), 6.57 ppm (s, 1-thiazole-H).

Further valuable active compounds, shown in the table which follows, can be prepared analogously to the preceding examples.

TABLE $$R_5-N\underset{\underset{O}{\|}}{\overbrace{\phantom{XXX}}}N-CONH-\underset{B}{CH}-CONH-\text{[penicillin]}$$

| R | B | R$_5$ | D |
|---|---|---|---|
| H | Furyl-2 | H | — |
| H | Furyl-2 | Methylsulphonyl | — |
| H | Furyl-2 | Cyclopropyl | — |
| H | Furyl-2 | Methylsulphonyl | C=O |
| OCH$_3$ | Furyl-2 | H | — |
| H | Furyl-3 | Methylaminosulphonyl | — |
| H | Furyl-3 | Cyclopropyl | — |
| OCH$_3$ | Furyl-3 | Cyclopropyl | — |
| H | Furyl-3 | Methylsulphonyl | C=O |
| H | Pyrrolyl-2 | H | — |
| OCH$_3$ | Pyrrolyl-2 | H | — |
| H | Pyrrolyl-2 | Methylsulphonyl | C=O |
| H | Pyrrolyl-2 | Cyclopropyl | — |
| H | Pyridinyl-3 | Methylaminosulphonyl | — |
| OCH$_3$ | Pyridinyl-3 | H | — |
| H | Pyridinyl-3 | Cyclopropyl | — |
| H | Pyridinyl-3 | Cyclopropyl | C=O |
| H | Pyridinyl-3 | Methylsulphonyl | — |
| H | Imidazolyl-2 | H | — |
| H | Imidazolyl-2 | Methylsulphonyl | — |
| OCH$_3$ | Imidazolyl-2 | Methylsulphonyl | — |
| H | Imidazolyl-2 | Methylsulphonyl | C=O |
| H | Imidazolyl-2 | Methylaminosulphonyl | — |
| H | 1-Methylimidazolyl-2 | H | — |
| H | 1-Methylimidazolyl-2 | Methylsulphonyl | — |
| OCH$_3$ | Isothiazolyl-5 | H | — |
| H | Isothiazolyl-5 | Methylsulphonyl | — |
| H | Isothiazolyl-5 | Methylaminosulphonyl | — |
| H | Thiazolyl-4 | H | — |
| H | Thiazolyl-4 | Methylsulphonyl | — |
| OCH$_3$ | Thiazolyl-4 | Methylaminosulphonyl | — |
| H | Thiazolyl-4 | H | C=O |
| H | 5-Methylisoxazolyl-3 | H | — |
| H | 5-Methylisoxazolyl-3 | Cyclopropyl | — |
| OCH$_3$ | 5-Methylisoxazolyl-3 | Cyclopropyl | — |
| H | 2-Imino-Δ$^4$-thiazolinyl-4 | Methylaminosulphonyl | — |
| OCH$_3$ | 2-Imino-Δ$^4$-thiazolinyl-4 | Cyclopropyl | — |
| H | 2-Imino-Δ$^4$-thiazolinyl-4 | Cyclopropyl | — |

Among the new β-lactam salts and esters of the invention, those salts and esters that are pharmaceutically acceptable are particularly important and are preferred.

The new free β-lactams of the general formula I and their salts and esters can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal or human being, is converted in the patient's body to the active compound.

It will be appreciated that the instant specification and examples are set forth by way of illustration and not limitation, and that various modifications and changes may be made without departing from the spirit and scope of the present invention.

What is claimed is:

1. A penicillin derivative of the formula

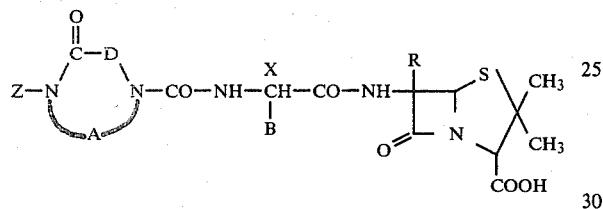

an ester or salt thereof, or a derivative thereof in which the carboxyl group is protected by a protective group, in which R denotes a hydrogen atom or a $C_1$-$C_6$-alkoxy group, B denotes furyl, pyrrolyl, pyrazolyl, imidazoly, triazolyl, tetrazolyl, oxazolyl, isoxazolyl, oxdiazolyl, thiazolyl, 2-imino-$\Delta^4$-thiazolin-4-yl, isothiazolyl, thiadiazolyl, oxtriazolyl, thiatriazolyl, sydnonyl, pyridyl, pyrazinyl, pyridazinyl, pyrimidinyl, triazinyl, tetrazinyl or pyronyl said heterocyclic groups being unsubstituted or substituted by halogen, $C_1$-$C_6$-alkyl, cyano, nitro, hydroxyl, amino, sulpho or methylsulfonyl, A denotes an ethylene, trimethylene or o-phenylene radical, D denotes a carbonyl group or a direct bond and Z denotes hydrogen, $C_1$-$C_6$-alkyl, $C_2$-$C_6$-alkenyl, $C_3$-$C_{10}$-cycloalkyl, $C_3$-$C_{10}$-cycloalkenyl or $C_3$-$C_{10}$-cycloalkadienyl, aralkyl with 6 or 10 carbon atoms in the aryl radical and 1 to 4 carbon atoms in the alkyl part, $C_6$-$C_{10}$-aryl, said alkyl, alkenyl, cycloalkyl, cycloalkenyl, cycloalkadienyl, aralkyl and alkyl being unsubstituted or substituted by $R_3$; thienyl, furyl, oxazolyl, isoxazolyl, thiazolyl, isothiazolyl, pyrrolyl, imidazolyl, pyrazolyl, oxadiazolyl, thiadiazolyl, triazolyl, oxtriazolyl, thiatriazolyl, tetrazolyl, pyridyl, pyrazinyl, pyrimidinyl, tetrahydrofuranyl, dioxanyl, pyrrolidinyl, piperidinyl, morpholinyl, pyron-2-yl or pyron-4-yl, said heterocyclic groups being unsubstituted or substituted by $C_1$ to $C_4$ alkyl, trifluoromethyl, halogen, amino, $C_1$ to $C_4$ alkylamino, di-($C_1$ to $C_4$ alkyl)-amino, formylamino, acetylamino, methoxycarbonylamino, ethoxycarbonylamino, methylsulphonylamino, hydroxy, methoxy, ethoxy, methylmercapto, ethylmercapto, methylsulphonyl, methylsulphinyl, carboxy, sulpho, formyl, ($C_1$ to $C_4$ alkyl)-carbonyl, ($C_1$ to $C_4$ alkoxy)-carbonyl or cyano, if the substituent is bonded to a carbon atom or substituted by $C_1$ to $C_4$ alkyl, cyano, formyl, ($C_1$ to $C_4$ alkoxy)-carbonyl, aminocarbonyl, ($C_1$ to $C_4$ alkylamino)-carbonyl, and $C_1$ to $C_4$ alkyl)-carbonyl, if the substituent is bonded to a nitrogen; ($C_1$ to $C_4$ alkyl)-carbonyl, phenylcarbonyl unsubstituted or substituted by $R_3$ $C_1$ to $C_4$ alkylsulphonyl, phenylsulphonyl, unsubstituted or substituted by $R_3$, ($C_1$ to $C_4$ alkoxy)-carbonyl, aminocarbonyl and aminosulphonyl, unsubstituted or substituted by $C_1$ to $C_4$ alkyl, and $R_3$ is halogen, amino, $C_1$ to $C_4$-alkylamino, di-($C_1$ to $C_4$ alkyl)-amino, pyrrolidyl, piperidyl, formylamino, ($C_1$ to $C_4$ alkyl)-carbonylamino, N-($C_1$ to $C_4$-alkyl)-formylamino, N-($C_1$ to $C_4$ alkyl)-($C_1$ to $C_4$ alkyl)-carbonylamino, di-($C_1$ to $C_4$ alkyl)-methylimino, $C_1$ to $C_4$ alkylsulphonylamino, N-$C_1$ to $C_4$ alkyl-$C_1$ to $C_4$ alkylsulphonylamino, hydroxysulphonylamino, N-$C_1$ to $C_4$ alkylhydroxysulphonylamino, amidino, di-($C_1$ to $C_4$ alkyl)-amino-methylimino, pyrrolidinylmethylimino, guanido, nitro, azido, hydroxy, $C_1$ to $C_4$ alkoxy, formyloxy, ($C_1$ to $C_4$ alkyl)-carbonyloxy, ($C_1$ to $C_4$ alkoxy)-carbonyloxy, aminocarbonyloxy, ($C_1$ to $C_4$ alkylamino)-carbonyloxy, di-($C_1$ to $C_4$ alkyl)-aminocarbonyloxy, piperidinylcarbonyloxy, aminosulphonyloxy, $C_1$ to $C_4$ alkylaminosulphonyloxy, di-($C_1$ to $C_4$ alkyl)-aminosulphonyloxy, carboxy, aminocarbonyl, di-($C_1$ to $C_4$ alkyl)-aminocarbonyl, formyl, hydroxysulphonyloxy, mercapto, $C_1$ to $C_4$ alkylmercapto, $C_1$ to $C_4$ alkylsulphinyl, sulpho, $C_1$ to $C_4$ alkylsulphonyl, aminosulphonyl, $C_1$ to $C_4$ alkylaminosulphonyl, di-($C_1$ to $C_4$ alkyl)-aminosulphonyl, piperidinylsulphonyl, thiosulphate, phenoxy and—in the case of the cyclic radicals—alkyl with 1 to 6 carbon atoms.

2. A compound according to claim 1, in which

A denotes an ethylene radical,

R denotes a hydrogen atom or a methoxy group and

B denotes a furyl, pyrrolyl, pyrazolyl, imidazolyl, thiazolyl, isothiazolyl, oxazolyl, isozazolyl, thiadiazolyl, oxdiazolyl, iminothiazolyl, pyridyl, pyrimidinyl, pyridazinyl, pyrazinyl, sydnonyl, tetrazolyl or 2-imino-$\Delta^4$-thiazolin-4-yl group.

3. A compound according to claim 1, in the form of the sodium salt.

4. A compound according to claim 1, in which

Z denotes a hydrogen atom or a methyl, ethyl, propyl, cyclopropyl, methylsulphonyl, ethylsulphonyl, phenylsulphonyl, methylaminosulphonyl or thiazolyl group.

5. A compound according to claim 1, wherein such compound is sodium 6-{α-[(2-oxo-imidazolidin-1-yl)-carbonylamino]-furyl-2-acetamido}-pencillinate of the formula

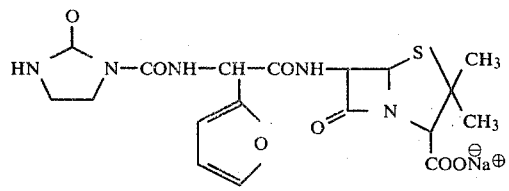

6. A compound according to claim 1, wherein such compound is sodium 6-{α-[(2-oxo-3-methylsulphonylimidazolidin-1-yl)-carbonylamino]-furyl-2-acetamido}-penicillinate of the formula

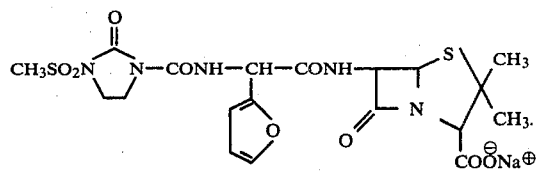

7. A compound according to claim 1, wherein such compound is sodium 6-{α-[(2-oxo-3-methylsulphonyl-imidazolidin-1-yl)-carbonylamino]-(5-methyl-isoxazol-3-yl)-acetamido}-pencillinate of the formula

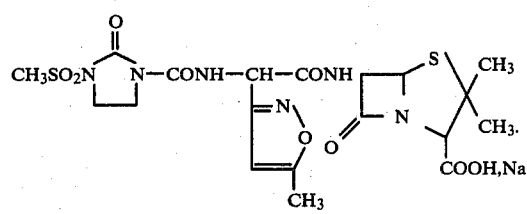

8. A compound according to claim 1, wherein such compound is sodium 6-{α-[(2,3-dioxo-4-ethyl-piperazin-1-yl)-carbonylamino]-furyl-2-acetamido}-penicillinate of the formula

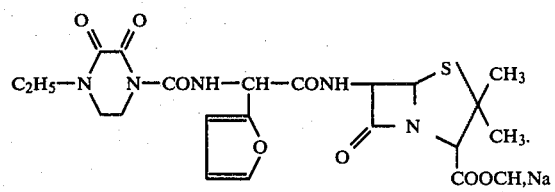

9. A compound according to claim 1, wherein such compound is sodium 6-{α-[(2-oxo-3-methyl-sulphonyl-imidazolin-1-yl)-carbonylamino]-(5-methyl-furyl-2-)acetamido}-penicillinate of the formula

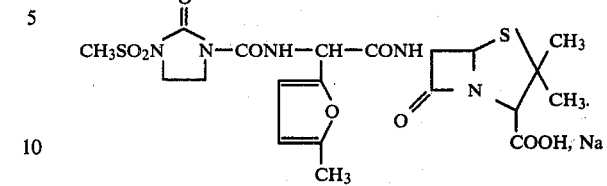

10. A compound according to claim 1, wherein such compound is sodium-6-{2-[(2-oxo-imidazolidin-1-yl)-carbonylamino]-2-(2-amino-thiazol-4-yl)-acetamido}-penicillinate of the formula

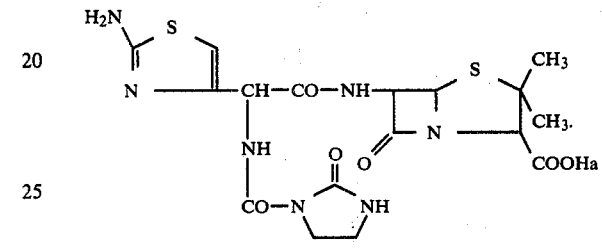

11. A compound according to claim 1, wherein such compound is sodium-6-{2[(2-oxo-3-methylsulfonyl-imidazolidin-1-yl)-carbonylamino]-2-(2-amino-thiazol-4-yl)-acetamido}-penicillinate of the formula

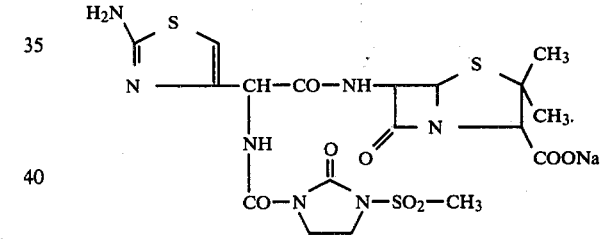

* * * * *

UNITED STATES PATENT AND TRADEMARK OFFICE
CERTIFICATE OF CORRECTION

PATENT NO.  : 4,235,774
DATED       : Nov. 25, 1980
INVENTOR(S) : Michael Preiss et al.

It is certified that error appears in the above—identified patent and that said Letters Patent is hereby corrected as shown below:

Abstract, Title page    In formula delete " x " and insert
$$-- \overset{CH}{\underset{CH}{*}} --.$$

Col. 21, line 25    In formula delete " x " and insert
$$-- \overset{CH}{\underset{CH}{*}} --.$$

Col. 24, line 24    Delete "COOHa" and insert --COONa--.

Signed and Sealed this

First Day of June 1982

[SEAL]

Attest:

GERALD J. MOSSINGHOFF

*Attesting Officer*    *Commissioner of Patents and Trademarks*